United States Patent [19]

Short et al.

[11] Patent Number: 5,188,957
[45] Date of Patent: Feb. 23, 1993

[54] LAMBDA PACKAGING EXTRACT LACKING BETA-GALACTOSIDASE ACTIVITY

[75] Inventors: Jay M. Short, Encinitas; Patricia Kretz, San Marcos, both of Calif.

[73] Assignee: Stratagene, La Jolla, Calif.

[21] Appl. No.: 661,396

[22] Filed: Feb. 26, 1991

Related U.S. Application Data

[63] Continuation-in-part of Ser. No. 661,439, Feb. 25, 1991, abandoned.

[51] Int. Cl.$^5$ .......................... C12N 7/06; C12N 1/21
[52] U.S. Cl. .......................... 435/235.1; 435/252.33; 435/69.1
[58] Field of Search ................ 536/27; 435/69.1, 239, 435/235.1, 252.33, 320.1

[56] References Cited

PUBLICATIONS

Frischauf, from *Methods in Enzymology* vol. 152, 1987, pp. 190–212.
Maniatis et al, *Molecular Cloning: A Laboratory Manual*, Cold Spring Harbor Laboratory, 1st ed., pp. 504–505, 1982.
Miller, *Experiments in Molecular Genetics*, Cold Spring Harbor Laboratory, Cold Spring Harbor, NY, 1972.
Hohn et al., *Proc. Natl. Acad. Sci. USA*, 74:3259–3263 (1977).
Maniatis et al., In Vitro Packaging of Bacteriophage λ DNA, 256–268.
Rosenberg et al., *Gene*, 38:165–175 (1985).

*Primary Examiner*—Richard A. Schwartz
*Assistant Examiner*—James Ketter
*Attorney, Agent, or Firm*—Thomas Fitting

[57] ABSTRACT

A beta-galactosidase-free bacteriophage lambda DNA packaging extract is described. The extract can be produced from beta-galactosidase deficient lambda lysogens. Bacteriophage lambda lysogens having the genotype lacZ are provided.

7 Claims, No Drawings

LAMBDA PACKAGING EXTRACT LACKING BETA-GALACTOSIDASE ACTIVITY

CROSS REFERENCE TO RELATED APPLICATIONS

This is a continuation-in-part of U.S. patent application Ser. No. 07/661,439, filed Feb. 25, 1991, now abandoned the disclosures of which are hereby incorporated by reference.

TECHNICAL FIELD

This invention relates to compositions and kits for packaging bacteriophage lambda DNA in vitro. More specifically, this invention contemplates a beta-galactosidase-free bacteriophage lambda DNA packaging extract.

BACKGROUND

Bacteriophage lambda DNA can be packaged in vitro using protein extracts prepared from bacteria infected with lambda phage lacking one or more genes for producing the proteins required for assembly of infectious phage particles. Typical in vitro packaging reactions are routinely capable of achieving efficiencies of 10a plaque from units (pfu) per $\mu$g of intact bacteriophage lambda DNA. About 0.05–0.5 percent of the DNA molecules present in the reaction can be package into infectious virions.

Various genetic mutations affect different stages of bacteriophage lambda DNA packaging. For instance, the E protein is the major component of the bacteriophage head and is required for the assembly of the earliest identifiable precursor. Bacteriophages mutant in the E gene (E$^-$) accumulate all of the components of the viral capsid. The D protein is localized on the outside of the bacteriophage head and is involved in the coupled process of insertion of bacteriophage lambda DNA into the "prehead" precursor and the subsequent maturation of the head. Bacteriophages mutant in the D gene (D$^-$) accumulate the immature prehead but do not allow insertion of bacteriophage lambda DNA into the head. The A protein is involved in the insertion of bacteriophage lambda DNA into the bacteriophage prehead and cleavage of the concatenated precursor DNA at the cos sites. Bacteriophages mutant in the A gene (A$^-$) also accumulate empty preheads. Complementing extracts have been prepared from cells infected with A. and E$^-$or D$^-$and E$^-$strains; alternatively, extracts prepared from cells infected with A. mutants can be complemented by the addition of purified wild-type A protein.

Of particular interest to the present invention is the packaging of bacteriophage lambda DNAs containing the E. coli beta-galactosidase gene (lacZ) and the E. coli gene that codes for the lacZ repressor (lacI). In such DNA's, a functional lacI represses expression of beta-galactosidase. However, when lacI is rendered non-functional, either through mutation or insertion of foreign DNA, lacZ expression, i.e., beta-galactosidase production, occurs.

The expression of beta-galactosidase can be used as a marker for host transformation. Detection usually involves exposing the putatively transformed host to the chromogenic substrate 5-bromo-4-chloro-3-indolyl-$\beta$-D-galactoside (x-gal) and visually screening for the formation of dark blue plaques against a white background.

SUMMARY

It has now been discovered that a residual amount of active beta-galactosidase copurifies with DNA packaging extracts prepared from bacteriophage lambda lysogens containing the beta-galactosidase (lacZ) gene. Thus, the present invention contemplates a bacteriophage lambda DNA packaging extract that is free of beta-galactosidase.

The extract is typically produced by isolating lambda DNA packaging proteins from beta-galactosidase deficient lambda lysogens. Useful lysogen genotypes provided by this invention include lacZ (A$^-$) lacZ (E$^-$) and lacZ (D$^-$). It is preferred that the lysogens have one or more of the following mutations: mcrA$^-$, mcrB$^-$, mrr$^-$, hsdR$^-$.

DETAILED DESCRIPTION OF THE INVENTION

The present invention contemplates a bacteriophage lambda DNA packaging extract that is free of beta-galactosidase. A bacteriophage lambda DNA packaging extract is a proteinaceous composition that is capable of packaging bacteriophage lambda DNa into infectious virus particles. Preferably, the lambda DNa packaging extracts of this invention having a packaging efficiency of at least $10^8$, and more preferably at least $10^9$, pfu/$\mu$g of intact lambda DNA.

The packaging extracts of this invention are usually prepared from cells containing beta-galactosidase deficient, i.e., lacZ, bacteriophage lambda lysogens of the appropriate genotype, e.g., amber mutations in genes A, D, E and the like. In addition to lacking a functional lacZ gene, useful lysogens preferably have one or more of the following mutations:

cIts857—specifies a temperature-sensitive bacteriophage lambda repressor molecule. This mutation causes lambda DNA to be maintained in the lysogenic state when the host bacteria are grown at 32° C.; bacteriophage growth is induced by transiently raising the temperature to 42°–45° C. to inactivate the repressor specified by the cI gene.

Sam7—an amber mutation in the bacteriophase S gene that is required for cell lysis. This mutation causes capsid components to accumulate within SuIII$^-$bacterial cells for 2–3 hours following induction of the cIts857 lysogen.

b-region deletion (b2 or b1007)—a deletion in the bacteriophage genome that effectively removes the lambda DNA attachment site (att). This mutation reduces, but does not entirely eliminate, the packaging of endogenous lambda DNA molecules in extracts made from the induced cells.

red3 (in lambda) and recA (in E. coli)—mutations that inactivate the generalized recombination systems of bacteriophage lambda and the host, thereby minimizing recombination between the endogenous lambda DNA in the extract and the exogenously added recombinant genomes.

The efficiency of a packaging extract is also dependent on whether or not the lambda lysogen (bacterium carrying a lambda prophage) contains a controlled restriction system. Host controlled restriction systems enable a bacterial cell to identify and inactivate foreign DNA by endonuclease cleavage. DNA is susceptible to restriction by the endonucleic activity of the host unless it is protected by modifications, such as methylation of specific nucleotides. While methylation of specific nucleotides usually serves to protect DNA from restriction by the endonucleolytic activity of the host, methylation at some DNA sequences actually confers sensitivity to restriction. One example, the mcrB restriction system of E. coli K-12, is responsible for the biological inactivation of foreign DNA that contains 5-methylcytosine residues. Ross et al., Journal of Bacteriology, 171:1974-1981 (1989).

There are a number of restriction/methylation systems endogenous to E. coli which are capable of inactivating foreign DNA by endonuclease cleavage. The most widely known systems are hsd i.e., EcoK, (Bickle, T. Nucleases, p. 85, Cold Spring Harbor Lab., Cold Spring Harbor, N.Y. 1982), mrr (Heitman, J. et al , J. Bacteriol. 169:3243-3250 (1987)), mcrA (Raleigh et al., PNAS, 83:9070-9074, (1986)) and mcrB (Raleigh, suora). The hsd system works by selectively restricting DNA that is not protected by adenine methylation at the N-6 position in the sequence, (SEQ ID NO 1) $A^{6-meA}$CNNNNNNGTGC or (SEQ IF NO 2) GC$^{6me}$ACNNNNNNGT. The mrr system also involves adenine methylation, however, in this case the methylation does not serve to protect the DNA, but serves to make the DNA vulnerable to the restriction system. The systems mcrA and mcrB are similar to mrr in that they recognize and restrict methylated DNA. However, these two systems differ from mrr in that they recognize methylated cytosine. Further, the mcrB function is provided by the products of at least two genes, mcrB and mcrC (Ross et al., J. Bacteriol., 171:1974-1981 (1989)). The recognition sequences for mcr and mrr are contemplated in the literature, but precise sequences are as yet unknown.

Thus, in preferred embodiments, the lacZ lambda lysogen is deficient in one or more of the mcrA, mcrB, hsd and mrr restriction systems. The genes comprising these systems can be removed or inactivated by well known methods, such as by transduction, transposon (Tn) mutagenesis, and the like.

Of course, one skilled in the art will recognize that "removal" of these restriction systems may be effected by deleting or inhibiting the activity of these restriction systems, and the term "restriction system deficient" includes, but is not limited to, removal of the restriction systems by either method. In addition, naturally occurring strains of E. coli that are deficient in these restriction systems may be isolated and used.

Exemplary bacterial strains are listed in Table 1 and are available from the following source of reference: ED8767 (Ishiura, M. et al., Anal. Biochem., 176:117-127 (1988); ER1451 (New England BioLabs, Beverly, Mass.); LCK8 (B. Bachman, Yale E. coli Center); NM621 (N. Murray, Univ. of Edinburgh); K802, LE392, NM554, PLK-A, PLK-17, Y1088, E. coli C, Sure (Stratagene, La Jolla, Calif.)).

TABLE 1

|         | hsdR | mcrA | mcrB | mrr |
|---------|------|------|------|-----|
| ED8767  | −    | −    | −    | +   |
| ER1451  | −    | −    | −    | +   |
| K802    | −    | −    | −    | +   |
| LCK8    | −    | −    | −    | +   |
| LE392   | −    | −    | +    | +   |
| NM554   | −    | −    | −    | +   |
| NM621   | −    | −    | −    | +   |
| PLK-A   | −    | −    | −    | +   |
| PLK-17  | −    | −    | −    | +   |

TABLE 1-continued

|           | hsdR | mcrA | mcrB | mrr |
|-----------|------|------|------|-----|
| Y1088     | −    | −    | +    | (+) |
| E. coli C | −    | −    | −    | −   |

Strains BHB2688R⁻ and BHB2690R⁻ are constructed using recA+ transformants of E. coli strains BHB2688 and BHB2690, respectively, as the recipients and any E. coli K-12 strain that carries a Tn10 (tetracycline resistant) in (or near) the mcrA gene (relevant genotype=mcrA:Tn10(tet$^R$)) as the donor. BHB2688, which is E⁻, and BHB2690, which is D⁻, are available from the American Type Culture Collection (ATCC), Rockville, Md. under the accession numbers 35131 and 35132, respectively. RecA+ transformation is accomplished by standard methods, typically using a recA expressing plasmid. Step 1: A P1 lysate is made from the E. coli K-12 strain described above. Step 2: BHB2688 and BHB2690 are transduced with the P1 lysate (Miller, J., Experiments in Molecular Genetics, Cold Spring Harbor Lab., Cold Spring Harbor, N.Y. (1972)). Step 3: Tetracycline (tet$^R$) resistant colonies are selected and purified. Step 4: Loss of tetracycline resistance is selected for on Bochner plates (Bochner, B. R., et al., J. Bacteriol., 143:926-933 (1980)), and colonies are purified. Step 5: Lack of mcrA restriction activity is tested by comparing transformation efficiency of unmethylated pBR322 versus pBR322 that has been in vitro methylated by HpaII methylase (Raleigh, supra). A mcrA+ strain will show a greatly reduced efficiency with the methylated plasmid. If mcrA activity is absent, this strain is then called BHB2688mcrA⁻ and BHB2690mcrA⁻.

To delete the mcrB locus in the above mcrA⁻ strains, a donor E. coli K-12 strain with the relevant genotypes mcrB::Tn10(tet$^R$), mrr::Tn5(kan$^R$) was used. Make a P1 lysate from an E. coli K-12 strain that carries a Tn10(tet$^R$) in the mcrB gene. The strain should also have a Tn5(kan$^R$) in the mrr gene. Step 7: Transduce the BHB2688 mcrA⁻ and BHB2690 mcrA⁻recA+(-tet$^S$) strain. Step 8: Select for tet$^R$ colonies. Purify one colony that is also kan$^R$. Step 9: Select for loss of tet$^R$ on Bochner plates (Bochner, supra). Step 10: Purify several colonies and test for sensitivity to tetracycline and kanamycin. Select colonies that are both tet$^S$ and kan$^S$. Step 11: Test for lack of McrB restriction activity as done for the mcrA test, however in this case, the pBR322 should be in vitro methylated by AluI methylase (Raleigh, supra: Ross, supra). A mcrB+ strain will show a greatly reduced efficiency with the methylated plasmid. Test for mrr restriction activity by comparing plating efficiency of lambda versus lambda which has been in vivo methylated by Pst I methylase (Heitman, supra). An mrr+ strain will show reduced efficiency with the methylated lambda. Test for hsdR restriction activity by comparing plating efficiency of lambda versus lambda which has been in vito methylated by hsdM methylase (Wood, W., J. Mol Biol., 16:118-133, (1966); Adams, Bacteriophages, N.Y.: Interscience 1959; Bickle, supra, at pp. 95-100). An hsdR+ strain will show reduced efficiency with unmethylated lambda. If a strain (purified colony) lacks all restriction activity mcrA, mcrB, mrr, hsdR and was constructed by this method, it should then contain a deletion throughout the mcrB region mcrB). These strains are BHB2688R⁻ and BHB2690R⁻.

Packaging extracts are usually prepared by growing the appropriate lacZ lysogenic bacteria to mid-log phase at 32° C., inducing lytic functions by inactivating the cI repressor protein by raising the temperature to 45° C. for 15 minutes, and then growing the cultures for an additional 2-3 hours at 38°-39° C. to allow packaging components to accumulate. Cell extracts are then prepared.

Usually two lysogens, e.g., A⁻ and E⁻ or D⁻ and E⁻, that provide complementing components of the packaging reaction are grown and induced separately. Extracts of each culture are prepared and blended into a mixture that contains all of the components necessary for packaging of bacteriophage lambda DNA. Neither lysogen alone is capable of packaging exogenously added DNA. The protocol is highly reproducible and simple, and it results in packaging mixtures that are efficient and free from background (when assayed on hosts that are nonsuppressing).

Alternatively, a single lacZ lysogenic strain of *E. coli* can be used to prepare the extract. A single lysogen can be used to prepare packaging extracts for two reasons. First, the bacteriophage lambda genome lysogenic in the strain codes for all of the proteins needed for packaging. Second, the cos site of the prophage has been deleted. These features work together in the following manner. Induction of the lysogen results in the intracellular accumulation of all protein components needed for packaging, and complete preheads are formed. However, the next steps in the packaging process are the recognition of the cos sites on concatenated bacteriophage lambda DNA by the bacteriophage A protein and the insertion of the bacteriophage lambda genome into the prehead. The lack of the cos site in the prophage DNA prevents this step from occurring, and packaging is thus effectively halted at the prehead stage, even though all necessary components that are used later in the process are present. Exogenous DNA with an active cos site is inserted into the prehead, and the packaging process then leads to the production of an infectious bacteriophage particle. Extracts made in this way usually have a lower background of plaques than the classical binary mixtures, because the deletion of the cos site blocks packaging of endogenous bacteriophage lambda DNA more completely than does the deletion of the b region.

*E. coli* C can be used as the host for the lysogen to lessen the probability of recombination between cryptic bacteriophage lambda prophages, which are known to be present in the genome of *E. coli* K, and the cos-deleted prophage. Furthermore, *E. coli* C lacks the EcoK restriction system (Rosenberg 1985). This system, like other restriction systems, cuts unmodified DNA in a sequence-specific manner and is also functional under the conditions of an in vitro packaging reaction. Thus, extracts prepared from cells of *E. coli* K have the potential to select against DNA that contains an unmodified EcoK recognition site. Because eukaryotic DNA used to construct libraries will not be protected from cleavage, clones that by chance contain an EcoK recognition site may be lost from the population during packaging. Reconstruction experiments show that bacteriophage lambda DNA carrying an EcoK recognition site is packaged two- to sevenfold less efficiently in extracts derived from *E. coli* K than in extracts prepared from *E. coli* C, Rosenberg et al., Gene, 38:165 (1985).

The reagents described herein can be packaged in kit form. As used herein, the term "package" refers to a solid matrix or material customarily utilized in a system and capable of holding within fixed limits one or more of the reagent components for use in a method of the present invention. Such materials include glass and plastic (e.g., polyethylene, polypropylene and polycarbonate) bottles, vials, paper, plastic and plastic-foil laminated envelopes and the like. Thus, for example, a package can be a glass vial used to contain the appropriate quantities of one or more bacteriophage lambda packaging proteins, such as those obtained from lambda lysogen strains lacZ (A⁻), lacZ (E⁻), lacZ (D⁻), and the like. An aliquot of each reagent sufficient to perform at least one in vitro packaging reaction will be provided in each container. In preferred embodiments, a kit will also contain aliquots of one or more of the following: an *E. coli* host for receiving lambda DNA packaged by the packaging reagent(s), control lambda DNA, X-gal, and the like.

EXAMPLES

The following examples are intended to illustrate, but not limit, the present invention.

1. Construction of *E. coli* RecA⁻ Lysogen Strains a. *E. coli* BHB2690R⁻

1) Transduction to Obtain BHB2690mcrA⁻ a) Preparation of a P1 Lysate

A bacteriophage P1 lysate, hereinafter referred to as P1, was made from any *E. coli* K12 strain that carries a tetracyline resistant Transposon 10 (Tn10) in or near the mcrA gene (Tn10::mcrA). Briefly, one drop from an overnight culture of K12 was admixed into 5 ml of LB broth (Luria-Bertani broth was prepared by admixing and dissolving 10 grams (g) bacto-tryptone, 5 g bacto-yeast extract and 10 g NaCl into 1 liter deionized water) containing $5 \times 10^{-3}$ molar (M) $CaCl_2$. The admixture was aerated by swirling until the cells were in exponential log phase growth and had reached a density of $2 \times 10^8$ a cells/ml P1 was preadsorbed by admixing $10^7$ phage to 1 ml of the above admixture followed by maintenance at 20 minutes in a 30 degrees Celsius (30° C.) waterbath to form a phage-cell admixture. LB-top agar, 2.5 ml, maintained at 45° C., was then admixed with the phage-cell admixture. The resultant agar-containing cell suspension was plated onto a freshly made LB plate which was maintained at 30° C. for 8 hours. At the end of the maintenance period, the soft agar layers was scraped into a small centrifuge tube. The scraped surface of the plate was then washed with 1 ml broth and the wash was collected for admixture with the scraped soft agar. Five drops of chloroform were added to the centrifuge tube followed by centrifugation to pellet cell debris. The resultant supernatant, containing the P1 lysate, was collected.

b) Transduction with P1 Lysates

In this invention, *E. coli* lysogen BHB2690 (ATCC # 35132) was used as the specific strain for transduction. *E. coli* BHB2690, which was RecA⁻, was first transformed with pJC859 to introduce a functional RecA protein into the lysogen. pJC859 was a plasmid in which the nucleotide sequence encoding RecA had been inserted at the Bam HI site of the plasmid *E. coli* vector, pBR322 (ATCC # 31344). Maniatis et al., *Molecular*

Cloning: A Laboratory Manual, Cold Spring Harbor Laboratory, 2nd ed., Sections 1.12 and 5.88, 1989; and U.S. Pat. No. 4843006 (in which the RecA promoter/operator and 150 amino acid residues of RecA coupled to a heterologous polypeptide sequence is described). For the transformation, E. coli BHB2690 competent cells were prepared following standard procedures familiar to one skilled in the art. Maniatis et al., supra, Section 1.76. Alternatively, competent cells can be obtained commercially.

Five ml of a fresh overnight culture of BHB2690 recA+ to be transduced was resuspended in 5 ml of buffer consisting of 0.1M $MgSO_4$ and 0.5mM $CaCl_2$ according to the procedure by Miller. Miller, *Experiments in Molecular Genetics*, Cold Spring Harbor Laboratory, 1972. The BHB2690 recA+ cell suspension was then aerated by swirling at 30° C. for 15 minutes. To each of 5 small test tubes, 0.1 ml of the aerated suspended cells was added. One hundred microliters (ul) of P1 lysate, prepared above, was added to the first tube. The P1 lysate was serially diluted 10-fold for addition to the remaining tubes except for the last tube which did not receive P1 and, thus, served as a control. A tube without cells containing P1 was also used as an additional control. The P1 lysate was preabsorbed by maintaining the tubes at 30° C. in a water bath for 20 minutes. Two hundred ul of 1M sodium citrate was then added to each of the prepared tubes and the contents of each tube was then plated on tetracycline-containing plates to select for tetracycline resistant ($tet^R$) colonies.

After maintaining the plates at 30° C. to allow for growth of colonies, $tet^R$ colonies were selected and purified following procedures well known to one skilled in the art. The $tet^R$ colonies were then replated on Bochner plates to select for the loss of tetR as described by Maloy. Maloy et al., *J. Bacteriol.*, 145:1110–1112 (1981). Briefly, tet-sensitive, $tet^S$, colonies were selected on a medium consisting of the following: 15 grams/liter (g/l) agar; 5 g/l tryptone broth; 5 g/l yeast extract; 4 milliliters/l (ml/1) chlortetracycline hydrochloride (12.5 milligram (mg)/ml); 10 g/l NaCl; 10 g/l $NaH_2PO_4$-$H_2O$; 6 ml/l fusaric acid (2 mg/ml); and 5 g/l $ZnCl_2$ (20 millimolar (mM)). Chemicals were obtained from Sigma. (Sigma, St. Louis, Mo.).

Selected $tet^S$ colonies were then purified and tested for the lack of mcrA restriction activity. The determination of mcrA− strains was accomplished by comparing transformation efficiency of unmethylated pBR322 versus pBR322 that had been in vitro methylated by Hpa II methylase. A mcrA+ strain showed a greatly reduced efficiency with the methylated plasmid. BHB2690RecA+mcrA−; hereinafter designated BHB2690mcrA−, strains were, thus, determined and used to make BHB2690mcrB− transductions as described below.

2) Transduction to Obtain BHB2690mcrB−

The BHB2690mcrA− strains prepared above were used in similar transductions to select for BHB2690mcrB− strains. For this procedure, a P1 lysate was prepared as described above from any E. coli K12 strain that carried a Tn10 ($tet^R$) in the mcrB gene (mcrB::Tn10 ($tet^R$)). The strain selected also carried the Tn5 with kanamycin (antibiotic) resistant gene ($kan^R$) in the mrr gene (mrr::Tn5 ($kan^R$)).

The E. coli BHB2690mcrA− ($tet^S$) strains were then transduced with P1 lysate [(mcrB::Tn10 ($tet^R$) and (mrr::Tn5 ($kan^R$)) as described in Example 1a above.

$Tet^R$ colonies that were also $kan^R$ were selected and purified. The loss of $tet^R$ on Bochner plates was measured as described above. Colonies that were both $tet^S$ and $kan^S$ after selection on Bochner plates were purified.

The lack of mcrB restriction activity was performed as described for determining the lack of mcrA activity with the exception that pBR322 was in vitro methylated by Alu I methylase. A mcrB+ strain showed a greatly reduced efficiency with the methylated plasmid. The test for mrr restriction activity was accomplished by comparing plating efficiency of lambda versus in vivo methylated lambda (by Pst I methylase). A mrr+ strain showed reduced efficiency with the methylated lambda. A separate test for hsdR restriction activity was also performed as the lack of activity confirmed the deletion of the entire mcrB region. The hsdR restriction activity test was performed by comparing plating efficiencies of lambda versus lambda which had been in vivo methylated by hsdM methylase. A hsdR+ strain showed reduced efficiency with the unmethylated lambda. With these tests, a selected colony which lacks all restriction activity, mcrA, mcrB, mrr, and hsdR, and constructed using this transduction approach was shown to contain a deletion throughout the mcrB region. This strain was designated BHB2690R− and used for lacZ-transductions as described in Example 2 below.

b. E. coli BHB2688R−

E. coli BHB2688 strains containing RecA+ but lacking mcrA, mcrB, mrr and hsdR were prepared using the approach described above for preparing E. coli BHB2690R−. For the transductions, E. coli lysogen BHB2688 (ATCC # 35131) was used. The resultant strain, designated BHB2688R−, was used in the construction of LacZ-transductants described in Example 3 below.

2. Construction of LacZ− Transductants—E. coli BHB2690RL−

The resultant transformed RecA+ E. coli lysogen, BHB2690R− prepared in Example 1 lacking mcrA, mcrB, mrr and hsdR, was then transduced with P1 as described by Miller. Miller, supra. The LacZ phenotype of all donor and recipient strains used for transductions was tested prior to use by separately streaking the selected strains on NZYM plates (NZYM is a medium prepared by admixing 10 g NZ amine, 5 g NaCl, 5 g bacto-yeast extract, and 2 g $MgSO_4$-$7H_2O$ into 1 liter of deionized water and adjusting the pH to 7.0 with 5.0N NaOH) on which an IPTG/X-Gal solution was spread (IPTG is isopropyl-beta-thio-galactopyranoside and X-Gal, is commercially available from Stratagene (Stratagene, La Jolla, Calif.); the solution was prepared by admixing 0.2M IPTG and 6 mg/ml X-Gal in a 50:50 mixture of DMSO and N,N-dimethlyformamide).

Briefly, a P1 lysate was prepared as described in Example 1 from the E. coli lacZ strain LE392.23. A similar E. coli strain, MC41000 (ATCC # 35695—F-delta(argF-Lac)(U169araD139)), can be used in preparing a P1 lacZ lysate for this invention. The transductions were performed as described in Example 1a and white transductants were selected on NZYM plates spread with IPTG/X-Gal as prepared above.

After screening 20,000 colonies, one white isolate was identified and purified on NZYM and reassayed for the lack of beta-galactosidase activity as described above. The resultant lacZ-derivatives of BHB2690R− were then grown at 30° C. in LB containing 5 to 10 ug/ml coumermycin Al to force the loss of the RecA+ plasmid, pJC859, according to the published procedures. Danilevskaya et al., *Mol. Gen. Genet.*, 178:233-235 (1980). Briefly, the antibiotic courmermycin which is an inhibitor of bacterial DNA gyrase was used to eliminate a plasmid such as pBR322 or in this case, pJC859. Courmermycin (Sigma) was dissolved in dimethylsulfoxide (1 mg/ml) (Sigma) and maintained at −10° C. An overnight culture of lacZ-derivatives of BHB2690R− was grown in LB at 30° C. The culture was then diluted in LB and plated for isolated colonies on NYZM. Following incubation of these plates overnight at 30° C., colony transfer pads were used to systematically transfer all colonies to fresh NZYM-ampicillin (antibiotic, amp) plates (100 ug/ml) and NZYM plates sequentially. Following an overnight incubation at 30° C., the sequential plates were then evaluated for the presence of amps colonies. The amp$^S$ colonies were then picked and purified.

Amp$^S$ derivative of BHB2690R− occurred at the rate of 1 to 380 colonies screened. The amp$^S$ phenotype of these isolates suggested that the recA+ plasmid had been deleted. To verify the recA− phenotype, a single streak of each isolate was placed on NZYM. One half of the plate was then exposed to 150 microjoules UV light in a Stratalinker (Stratagene). The lack of growth when exposed to the UV light verified the recA− condition of the isolates. The recA− isolates were then further screened phenotypically to verify that they were true derivatives of the original lysogenic strains and still carried the desired traits (lacking mcrA, mcrB, mrr, hsDA, lacZ and recA). The resultant isolate was designated BHB2690RL− and was used in the preparation of extract for prehead as described in Example 4a.

3. Construction of LacZ− Transductants—*E. coli* BHB2688RL−

The resultant transformed recA + *E. coli* lysogen, BHB2688R− prepared in Example 1b lacking mcrA, mcrB, mrr and hsdR, was then transduced with Pl as described by Miller. Miller, supra. The LacZ phenotype of all donor and recipient strains used for transductions was tested prior to use as described above.

Briefly, a Pl lysate was prepared as described in Example 1 from the lacZ strain NK5661. The strain, LE392.23 was initially used as the transducing strain but no lacZ transductants were obtained. Either CY15070 (ATCC #47022—lac Zu 118::Tn10) or NK5661 (is equivalent to strain W3110 (ATCC #27325) +Tn10—lacZ950::Tnl?) was used in the transductions instead of LE 392.23 which allowed for a direct and more efficient selection of lacZ− transductants due to the Tn10 (tet$^R$) within the lacZ gene. Three ×10$^8$ a cells were used for the transduction in a final volume of 1 ml which contained approximately 2000 lacZ::Tn10 (tet$^R$) transductants. After selection on NZYM-tetracycline plates, a transductant was purified and assayed for beta-galactosidase activity as described in Example 2 above. The selected isolate which lacked beta-galactosidase activity was then selected for loss of tet$^R$ by plating on Bochner plates as described in Example 1. This allowed for the isolation of a tet$^S$, lacZ− derivative of BHB2668R−.

The tet$^S$, lacZ− derivative of BHB2668R− was then grown in the presence of courmermycin as described for BHB2690R− to eliminate the pJC859 plasmid (Example 2). Ampicillin selection was also performed as described with the amp$^S$ derivatives of BHB2688R− occurring at the rate of 1 in 100 colonies screened. Verification of RecA− isolates that also lacked mcrA, mcrB, mrr, hsdR, and lacZ was performed as described in Example 2. The resultant isolate was designated BHB2688RL− and was used in the preparation of extract for protein donor as described in Example 4b.

4. Preparation of Packaging Extracts from Two Lysogens a. Preparation of Sonicated Extract from Induced *E.coli* Strain BHB2690RL− Cells For preparing a sonicated extract of the *E. coli* lysogen, strain BHB2690RL− (prehead donor) prepared in Example 2, the genotype of the strain is first verified before large-scale culturing. The presence of the mutation that renders the bacteriophage cI gene product temperature-sensitive is determined by streaking from the master stocks of *E. coli* BHB2690RL- onto two LB agar plates. One of the plates is maintained at 32° C. while the other is maintained at 45° C. Bacteria with intact an intact only grow on the plates maintained at 32° C. A single small colony of *E. coli* BHB2690RL− is picked and maintained overnight at 32° C. and 45° C. The bacteria with the mutation only grow at 32° C. and grow slowly due to the recA− mutation present in the BHB strains. A 100 ml subculture of the verified master stock of *E. coli* strain BHB2690RL− is then prepared and maintained overnight at 32° C.

After maintaining the *E. coli* BHB2690RL− culture overnight, the optical density (OD) is measured at a wavelength of 600 nm. An aliquot of the overnight culture is admixed into 500 ml of NZM broth (NZM broth is prepared by admixing 10 g NZ amine, 5 g NaCl, and 2 g MgSO$_4$-7H$_2$O to 950 ml of deionized water; the pH of the solution containing dissolved solutes is adjusted to pH 7.0 with 5 N NaOH), prewarmed to 32° C., in a 2-liter flask, to result in a starting OD$_{600}$ of approximately 0.1. The bacterial admixture is then maintained at 32° C. with vigorous agitation (300 cycles/minute in a rotary shaker) until an OD$_{600}$ of approximately 0.3 is reached. The OD$_{600}$ of 0.3 is generally attained within 2 to three hours of maintaining the culture. The cultures must be in the mid-log phase of growth prior to induction as described below.

The lysogen is induced by placing the flask in a water bath preheated to 45° C. The flask is swirled continuously for 15 minutes. An alternative approach for inducing lysogen is to immerse the flask in a shaking water bath set at 65° C. The temperature of the fluid contents of the flask is monitored. When the fluid reaches 45° C., the flask is then transferred to a water bath set at 45° C. and maintained for 15 minutes. The induced cells are then maintained for 2 to 3 hours at 38° to 39° C. with vigorous agitation as described above. A successful induction is verified by the visual clearance of an added drop of chloroform to the culture.

Following the 2 to 3 hour maintenance period, the cells are recovered from the admixture by centrifugation at 4000 g for 10 minutes at 4° C. The resultant supernatant is decanted and any remaining liquid is removed with a pasteur pipette and a cotton swab. The walls of the centrifuge bottle are wiped dry with towels. To the pelleted induced bacterial cells, 3.6 ml of freshly prepared sonication buffer is admixed. Sonication buffer consists of 20 mM Tris-HCl, pH 8.0, (Tris[hydroxymethyl]-aminomethane hydrochloride), 1 mM EDTA, pH 8.0, (ethylenediaminetetraacetic acid) and 5 mM beta-mercaptoethanol. The bacterial cell pellet is resuspended in the sonication buffer by mixing to form a homogenized cell suspension.

The resultant suspension is transferred to a small, clear plastic tube (Falcon 2054 or 2057, Falcon, Oxnard, Calif.) for subsequent sonication. The cells are disrupted by sonication with 10 second bursts at maximum power using a microtip probe. For sonication, the tube containing the suspension is immersed in ice water and the temperature of the sonication buffer should not be allowed to exceed 4° C. The sample is cooled for 30 seconds in between each sonication burst. The sonication procedure is continued until the solution in the tube clears and its viscosity decreases. The sonicated bacterial sample is transferred to a centrifuge tube and debris is pelleted by centrifugation at 12,000 g for 10 minutes at 4° C. forming a clear supernatant.

The resultant supernatant containing preheads is removed and admixed with an equal volume of cold sonication buffer and one-sixth volume of freshly prepared packaging buffer to form a diluted prehead admixture. Packaging buffer consists of the following: 6 mM Tris-HCl, pH 8.0; 50 mM spermidine; 50 mM putrescine; 20 mM $MgCl_2$; 30 mM ATP, pH 7.0; and 30 mM beta-mercaptoethanol. The admixture is then dispensed into pre-cooled to 4° C. 1.5-ml microfuge tube in 15 ul aliquots. The caps of the microfuge tubes are then closed and the tubes are immersed briefly in liquid nitrogen for freezing. The frozen preheads in packaging buffer are then stored at −70° C. for long-term storage.

b. Preparation of Frozen-Thawed Lysate of Induced *E. coli* BHB2688RL− Cells

A subculture of *E. coli* BHB2688RL−, prepared in Example 3 above, for obtaining an extract of packaging protein donor is verified for the genotype and is prepared as described above for preparing *E. coli* BHB2690RL−. Overnight cultures are maintained and lysogen is induced also as described above.

The induced *E. coli* BHB2688RL− cells are pelleted by centrifugation at 4000 g for 10 minutes at 4° C. The resultant supernatant is removed and any excess liquid is removed. The pelleted cells are resuspended in a total of 3 ml of ice-cold sucrose solution (10% sucrose in 50 mM Tris-HCl, pH 8.0) to form a cell suspension. The resultant cell suspension is dispensed in 0.5 ml aliquots into each of six precooled to 4° C. microfuge tubes. Twenty-five ul of fresh, ice-cold lysozyme solution (2 mg/ml lysozyme in 10 mM Tris-HCl, pH 8.0) is admixed to each tube containing the cell suspension. The cell-lysozyme admixture is gently mixed to form an *E. coli* extract and then immersed in liquid nitrogen for freezing.

The frozen tubes are removed from the liquid nitrogen and the extracts are thawed on ice. Twenty-five ul of packaging buffer, as prepared above, is admixed to each tube containing thawed extract to form a packaging buffer-extract admixture. The separately prepared admixtures are then combined in a centrifuge tube and centrifuged at 45,000 g for 1 hour at 4° C. to form an supernatant containing packaging protein donor.

The resultant supernatant is removed and dispensed in 10 ul aliquots into precooled at 4° C. microfuge tubes. The caps of the tubes are closed and the tubes are then immersed in liquid nitrogen. The tubes are then removed from the liquid nitrogen and stored at −70° C. for long term storage.

5. Preparation of In Vitro Packaging Using Two Extracts

The frozen tubes containing prehead and packaging donor extracts prepared in Example 4a and 4b, respectively, are removed from storage at −70° C. and allowed to thaw on ice. The frozen-thawed lysate containing the protein donor thaws first and is admixed to the still-frozen sonicated prehead extract to form a prehead-protein donor admixture. The resultant admixture is mixed gently until almost totally thawed. The DNA to be packaged (up to 1 ug dissolved in 5 ul of 10 mM Tris-HCl, pH 8.0, 10 mM $MgCl_2$) is admixed with the thawed combined extracts and mixed with a fine glass stirring rod to form a DNA-extract admixture. The admixture is then maintained for 1 hour at room temperature. To the admixture, 0.5 to 1 ml of SM (SM buffer is prepared by admixing 5.8 g NaCl, 2 g $MgSO_4\cdot7H_2O$, 50 ml Tris-HCl, pH 7.5, and 5 ml 2% gelatin (w/v) to 1 liter of deionized water and adjusting the pH to 7.5) and a drop of chloroform is added and gently mixed. Debris is removed by centrifugation at 12,000 g for 30 seconds at room temperature in a microfuge. The resultant supernatant is removed and contains packaged bacteriophage DNA particles.

The titer of the viable bacteriophage particles is measured by plating on the appropriate indicator strains. Recombinant DNAs that are 90% or 80% of wild-type bacteriophage lambda in length are packaged with efficiencies that are 20-fold to 50-fold lower, respectively, than those obtained with unit-length bacteriophage lambda. The same packaging extracts may be used for the packaging of both bacteriophage lambda and cosmids.

The foregoing is intended as illustrative of the present invention but not limiting. Numerous variations and modifications can be effected without departing from the true spirit and scope of the invention.

What is claimed is:

1. A bacteriophage lambda DNA packaging extract free of beta-galactosidase.

2. An aqueous composition of bacteriophage lambda DNA packaging proteins characterized as being free of beta-galactosidase and having a bacteriophage lambda DNA packaging efficiency of at least $10^8$ pfu/mg of intact bacteriophage lambda DNA.

3. A bacteriophage lambda lysogen having the genotype lacZ (A−).

4. A bacteriophage lambda lysogen having the genotype lacZ (E−).

5. A bacteriophage lambda lysogen having the genotype lacZ (D−).

6. A kit for packaging bacteriophage lambda DNA in vitro comprising an enclosure containing, in separate packages, a first extract of bacteriophage lambda packaging proteins from a lacZ ($E^{31}$) bacteriophage lambda lysogen, and a second extract of bacteriophage lambda packaging proteins from a lacZ (D−); or lacZ (A−) bacteriophage lambda lysogen, said first and second extracts forming, in admixture, a bacteriophage lambda DNA packaging extract.

7. The kit of claim 6 further containing, in a separate package, a lacZ E. coli host capable of being transformed by lambda DNA packaged by said bacteriophage lambda DNA packaging extract.

* * * * *

SEQUENCE LISTING ( 1 ) GENERAL INFORMATION:

( i i i ) NUMBER OF SEQUENCES: 2

( v i ) CURRENT APPLICATION DATA:
        ( A ) APPLICATION NUMBER: US 07/661,396
        ( B ) FILING DATE: 26-FEB-1991

( 2 ) INFORMATION FOR SEQ ID NO:1:

( i ) SEQUENCE CHARACTERISTICS:

(A) LENGTH: 13 base pairs
            (B) TYPE: nucleic acid
            (C) STRANDEDNESS: double
            (D) TOPOLOGY: linear (ii) MOLECULE TYPE: DNA (genomic)

(ix) FEATURE:
            (A) NAME/KEY: modifiedbase
            (B) LOCATION: 2
            (C) IDENTIFICATION METHOD: experimental
            (D) OTHER INFORMATION: /evidence=EXPERIMENTAL
                    / modbase=m6a (xi) SEQUENCE DESCRIPTION: SEQ ID NO:1:

AACNNNNNNG TGC                                                                                  13

(2) INFORMATION FOR SEQ ID NO:2:

(i) SEQUENCE CHARACTERISTICS:
            (A) LENGTH: 13 base pairs
            (B) TYPE: nucleic acid
            (C) STRANDEDNESS: double
            (D) TOPOLOGY: linear (ii) MOLECULE TYPE: DNA (genomic)

(ix) FEATURE:
            (A) NAME/KEY: modifiedbase
            (B) LOCATION: 3
            (C) IDENTIFICATION METHOD: experimental
            (D) OTHER INFORMATION: /evidence=EXPERIMENTAL
                    / modbase=m6a (xi) SEQUENCE DESCRIPTION: SEQ ID NO:2:

GCACNNNNNN GTT                                                                                  13